United States Patent
Petch et al.

(10) Patent No.: US 11,776,672 B1
(45) Date of Patent: Oct. 3, 2023

(54) SYSTEM AND METHOD FOR DYNAMICALLY SCORING DATA OBJECTS

(71) Applicant: Express Scripts Strategic Development, Inc., St. Louis, MO (US)

(72) Inventors: John C. Petch, St. Louis, MO (US); Billeigh Barackman, Troy, IL (US); Stephen J. Bergner, Chesterfield, MO (US); Christopher Greer, Lake St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 118 days.

(21) Appl. No.: 17/123,559

(22) Filed: Dec. 16, 2020

(51) Int. Cl.
*G16H 10/00* (2018.01)
*G16H 20/10* (2018.01)
*G16H 15/00* (2018.01)
*G16H 40/20* (2018.01)

(52) U.S. Cl.
CPC .............. *G16H 20/10* (2018.01); *G16H 15/00* (2018.01); *G16H 40/20* (2018.01); *G16H 10/00* (2018.01)

(58) Field of Classification Search
None
See application file for complete search history.

(56) References Cited

U.S. PATENT DOCUMENTS

| | | | |
|---|---|---|---|
| 5,535,322 A | 7/1996 | Hecht | |
| 7,069,509 B2 | 6/2006 | Griffin | |
| 7,225,272 B2 | 5/2007 | Kelley | |
| 7,493,295 B2 | 2/2009 | Ayala | |
| 7,707,032 B2 | 4/2010 | Wang | |
| 8,718,144 B2 | 5/2014 | Reznik | |
| 9,319,685 B2 | 4/2016 | Reznik | |
| 9,483,462 B2 | 11/2016 | Ikawa | |
| 9,550,986 B2 | 1/2017 | Dong | |
| 9,602,371 B2 | 3/2017 | Morris | |
| 9,679,030 B2 | 6/2017 | Hatami-Hanza | |
| 9,778,929 B2 | 10/2017 | Joo | |
| 9,779,189 B2 | 10/2017 | Maddala | |
| 9,979,748 B2 | 5/2018 | O'Connor | |
| 10,143,908 B2 | 12/2018 | Butler | |
| 10,332,617 B2 | 6/2019 | Kiel | |
| 2006/0224479 A1* | 10/2006 | Bishop | G06Q 40/06 705/35 |
| 2007/0208877 A1 | 9/2007 | Kelley | |
| 2010/0057645 A1* | 3/2010 | Lauritsen | G06N 5/042 706/11 |

(Continued)

FOREIGN PATENT DOCUMENTS

GB 2356718 B 11/2001

*Primary Examiner* — Xuyang Xia
(74) *Attorney, Agent, or Firm* — Dickinson Wright PLLC

(57) ABSTRACT

A method for dynamically scoring aspects of a data object includes receiving a first data object indicating and determining a first sum of a product of a first value and a first weight value plus a product of a second value and a second weight value and generating a first score based on a result of the first sum. The method also includes determining a second sum of a product of a third value and a third weight value plus a product of a fourth value and a fourth weight value and generating a second score based on a result of the second sum. The method also includes determining a first data object score for the first data object based on, at least, the first score, the second score, and a fifth value.

16 Claims, 10 Drawing Sheets

(56) References Cited

U.S. PATENT DOCUMENTS

| | | |
|---|---|---|
| 2013/0024395 A1 | 1/2013 | Clark |
| 2014/0012504 A1 | 1/2014 | Ben-Dor |
| 2014/0114674 A1* | 4/2014 | Krughoff ............... G06Q 10/10 |
| | | 705/2 |
| 2014/0279751 A1 | 9/2014 | Ram |
| 2014/0280353 A1 | 9/2014 | Delaney |
| 2015/0161629 A1 | 6/2015 | Verma |
| 2015/0199386 A1 | 7/2015 | Stokes |
| 2015/0254754 A1* | 9/2015 | Lang ...................... G06Q 40/08 |
| | | 705/4 |
| 2016/0078115 A1 | 3/2016 | Battista, Jr. |
| 2017/0270416 A1 | 9/2017 | Sri |
| 2017/0337632 A1 | 11/2017 | Dombek |
| 2018/0234490 A1 | 8/2018 | Moss |
| 2019/0087538 A1 | 3/2019 | Lim |
| 2019/0102710 A1 | 4/2019 | Predescu |
| 2019/0188109 A1 | 6/2019 | Yu |
| 2019/0244110 A1 | 8/2019 | Qiu |
| 2019/0352695 A1 | 11/2019 | Abdueva |
| 2019/0362847 A1 | 11/2019 | Dong |
| 2020/0005153 A1 | 1/2020 | Ramanath |
| 2020/0051451 A1 | 2/2020 | Goyal |
| 2020/0082359 A1 | 3/2020 | Xu |
| 2020/0352518 A1* | 11/2020 | Lyman ................. A61B 6/5258 |
| 2021/0065091 A1* | 3/2021 | Bhattacharyya ............................ |
| | | G06Q 10/06393 |
| 2021/0334664 A1 | 10/2021 | Li |

\* cited by examiner

| PROJECT | VALUE | WEIGHT | DOMAIN 1-WEIGHT | DOMAIN 2-WEIGHT | DOMAIN 3-WEIGHT | FIRST DATA OBJECT COMBINATION | DOMAIN 1-WEIGHT | DOMAIN 2-WEIGHT | DOMAIN 3-WEIGHT | VALUE REALIZED |
|---|---|---|---|---|---|---|---|---|---|---|
| DATA OBJECT 1 | $100 | $6 | $5 | $1 | $0 | 0 | $0 | $0 | $0 | $0 |
| DATA OBJECT 2 | $200 | $3 | $1 | $1 | $1 | 1 | $1 | $1 | $1 | $200 |
| DATA OBJECT 3 | $300 | $4 | $4 | $0 | $0 | 0 | $0 | $0 | $0 | $0 |
| DATA OBJECT 4 | $400 | $3 | $0 | $3 | $0 | 0 | $0 | $0 | $0 | $0 |
| DATA OBJECT 5 | $500 | $1 | $0 | $0 | $1 | 0 | $0 | $0 | $0 | $0 |
| | | | | | | TOTAL | $1 | $1 | $1 | $200 |
| | | | | | | DOMAIN BUDGET | $4 | $4 | $4 | |
| | | | | | | DOMAIN CONSTRAINTS MET? | YES | YES | YES | |

*FIG. 4A*

| PROJECT | VALUE | WEIGHT | DOMAIN 1-WEIGHT | DOMAIN 2-WEIGHT | DOMAIN 3-WEIGHT | FIRST DATA OBJECT COMBINATION | DOMAIN 1-WEIGHT | DOMAIN 2-WEIGHT | DOMAIN 3-WEIGHT | VALUE REALIZED |
|---|---|---|---|---|---|---|---|---|---|---|
| DATA OBJECT 1 | $100 | $6 | $5 | $1 | $0 | 0 | $0 | $0 | $0 | $0 |
| DATA OBJECT 2 | $200 | $3 | $1 | $1 | $1 | 1 | $1 | $1 | $1 | $200 |
| DATA OBJECT 3 | $300 | $4 | $4 | $0 | $0 | 0 | $0 | $0 | $0 | $0 |
| DATA OBJECT 4 | $400 | $3 | $0 | $3 | $1 | 1 | $0 | $3 | $0 | $400 |
| DATA OBJECT 5 | $500 | $1 | $0 | $0 | $1 | 1 | $0 | $0 | $1 | $500 |
| TOTAL | | | | | | | $1 | $4 | $2 | $1,100 |
| DOMAIN BUDGET | | | | | | | $4 | $4 | $4 | |
| DOMAIN CONSTRAINTS MET? | | | | | | | YES | YES | YES | |

SYSTEM AND METHOD FOR DYNAMICALLY SCORING DATA OBJECTS

TECHNICAL FIELD

This disclosure relates to data object management, and in particular to systems and methods for dynamically scoring data objects.

BACKGROUND

Medications, such as prescription medications, over-the-counter medications, vitamins, supplements, and the like, are increasingly being delivered by a medication provider, such as a large volume pharmacy and the like, to a residence or other location of an individual requiring such medications. Medications may be delivered using a variety of delivery services, such as a postal service, a parcel delivery service, a contractor, or other service under direct control of a corresponding medication provider, and the like.

Management of such a medication provider, such as management of the delivers, management of safety regulations corresponding to the storage and distribution of various pharmacological materials, management of a workforce supporting the medication provider, management of other various systems of the medication provider, and the like, may require various program and project management systems and methods. Typically, such program and project management systems and methods compete for resources during the same or substantially overlapping periods. Additionally, or alternatively, use of such management systems and methods may result in tangible and/or intangible benefit to the medication provider. Such tangible and/or intangible benefits may vary for individual ones of the management systems and methods.

SUMMARY

This disclosure relates generally to dynamically scoring data objects.

An aspect of the disclosed embodiments includes a system for dynamically scoring aspects of a data object. The system includes a processor and a memory. The memory includes instructions that, when executed by the processor, cause the processor to: receive a first data object indicating: a first value associated with a first value type, the first value corresponding to a first weight value; a second value associated with the first value type, the second value corresponding to a second weight value; a third value associated with a second value type, the third value corresponding to a third weight value; a fourth value associated with the second value type, the fourth value corresponding to a fourth weight value; and a fifth value corresponding to a third value type; determine a first sum of a product of the first value and the first weight value plus a product of the second value and the second weight value; generate a first score based on a result of the first sum divided by a sum of the first weight value and the second weight value; determine a second sum of a product of the third value and the third weight value plus a product of the fourth value and the fourth weight value; generate a second score based on a result of the second sum divided by a sum of the third weight value and the fourth weight value; and determine a first data object score for the first data object based on, at least, the first score, the second score, and the fifth value.

Another aspect of the disclosed embodiments includes a method for dynamically scoring aspects of a data object. The method includes receiving a first data object indicating: a first value associated with a first value type, the first value corresponding to a first weight value; a second value associated with the first value type, the second value corresponding to a second weight value; a third value associated with a second value type, the third value corresponding to a third weight value; a fourth value associated with the second value type, the fourth value corresponding to a fourth weight value; and a fifth value corresponding to a third value type. The method also includes determining a first sum of a product of the first value and the first weight value plus a product of the second value and the second weight value and generating a first score based on a result of the first sum divided by a sum of the first weight value and the second weight value. The method also includes determining a second sum of a product of the third value and the third weight value plus a product of the fourth value and the fourth weight value and generating a second score based on a result of the second sum divided by a sum of the third weight value and the fourth weight value. The method also includes determining a first data object score for the first data object based on, at least, the first score, the second score, and the fifth value.

Another aspect of the disclosed embodiments includes an apparatus for dynamically scoring aspects of a data object. The apparatus includes a processor and a memory. The memory includes instructions that, when executed by the processor, cause the processor to: receive a first data object indicating: a first value associated with a first value type, the first value corresponding to a first weight value; a second value associated with the first value type, the second value corresponding to a second weight value; a third value associated with a second value type, the third value corresponding to a third weight value; a fourth value associated with the second value type, the fourth value corresponding to a fourth weight value; and a fifth value corresponding to a third value type, the fifth value corresponding to an amount of effort associated with execution of a project associated with the first data object; determine a first sum of a product of the first value and the first weight value plus a product of the second value and the second weight value; generate a first score based on a result of the first sum divided by a sum of the first weight value and the second weight value; determine a second sum of a product of the third value and the third weight value plus a product of the fourth value and the fourth weight value; generate a second score based on a result of the second sum divided by a sum of the third weight value and the fourth weight value; determine a first data object score for the first data object based on, at least, the first score, the second score, and the fifth value; and generate a report comprising, at least, the first data object score and at least one other data object score, wherein the first data object score and the at least one other data object are organized on the report according to a dynamically generated order.

These and other aspects of the present disclosure are disclosed in the following detailed description of the embodiments, the appended claims, and the accompanying figures.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 1A generally illustrates a functional block diagram of a system including a high-volume pharmacy according to the principles of the present disclosure.

FIGS. 4A-4C generally illustrate data object combinations according to the principles of the present disclosure.

DETAILED DESCRIPTION

Figure 1A:
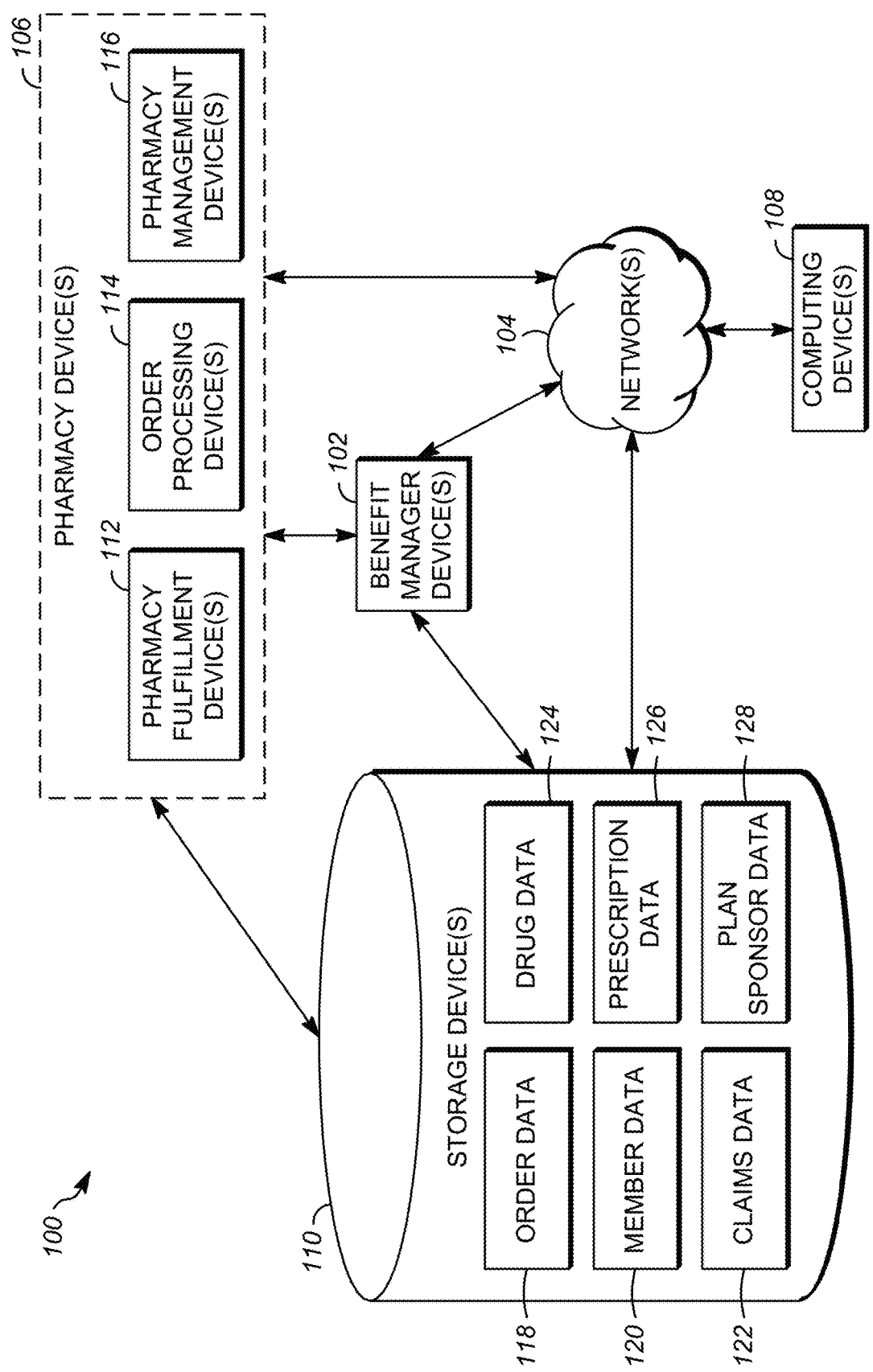
FIG. 1B generally illustrates a computing device according to the principles of the present disclosure.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As described, medications, such as prescription medications, over-the-counter medications, vitamins, supplements, and the like, are increasingly being delivered by a medication provider, such as a large volume pharmacy and the like, to a residence or other location of an individual requiring such medications. Medications may be delivered using a variety of delivery services, such as a postal service, a parcel delivery service, a contractor, or other service under direct control of a corresponding medication provider, and the like.

Management of such a medication provider, such as management of the delivers, management of safety regulations corresponding to the storage and distribution of various pharmacological materials, management of a workforce supporting the medication provider, management of other various systems of the medication provider, and the like, may require various program and project management systems and methods Such program and project management systems and methods compete for resources during the same or substantially overlapping periods. For example, various projects may be initiated to implement, upgrade, or otherwise utilize various management systems and methods. Such projects may utilize one or more domains (e.g., groups of workforce resources specializing in one or more technological or other area of expertise) to implement, upgrade, or otherwise utilize one or more of the various management systems and methods. Further, such projects may have associated capital or other resource costs, including, but not limited to, domain usage costs. Additionally, or alternatively, use of such management systems and methods may result in tangible and/or intangible benefit to the medication provider. Such tangible and/or intangible benefits may vary for individual ones of the management systems and methods.

Typically, various stakeholders within the medication provider organization may review such project costs and benefits and decide which project or group of projects should move forward, given various constraints (e.g., budget constraints, time constraints, resource constraints, etc.). Such decisions tend to be made using manual review of various information corresponding to the various projects. Additionally, such manual review by the various stakeholders may be biased and time consuming, and, in some cases, may lack critical information and/or analysis, which may render the decision making suboptimal.

According, systems and methods, such as those described herein, configured to dynamically score such projects and/or identify groups of projects that can be undertaken given various constraints, may be desirable. In some embodiments, the systems and methods described herein may be configured to provide dynamic common value scoring of the various projects. The systems and methods described herein may be configured to provide data-driven value prioritization of the various projects. The systems and methods described herein may be configured to provide enterprise-ranked opportunity canvases (e.g., reports and/or other data output). The systems and methods described herein may be configured to provide cost calculations, capacity constraint planning, data analysis, and the like for the various projects. The systems and methods described herein may be configured to provide preliminary impact analysis for the various projects. The systems and methods described herein may be configured to provide optimized project combination planning.

In some embodiments, the systems and methods described herein may be configured to simulate all variations of how the various projects can be sequenced. It should be understood that, while limited examples of medication providers, such as a high volume pharmacy, are described herein, the principles of the present disclosure are applicable to any suitable application, such as military strategy planning, software rollout planning, vehicle model rollout planning, vaccine development planning, vaccine manufacturing planning, vaccine distribution planning, and the like. Additionally, or alternatively, it should be understood that, while projects are described herein, the principles of the present disclosure apply to any suitable input. The systems and methods described herein may be configured to return or provide a most valuable or a substantially most valuable combination of projects for a given project timeframe. The systems and methods described herein may be configured to generate recommendations used by members of one or more domains to provide cross-functional domain output.

In some embodiments, the systems and methods described herein may be configured to receive project information input. The project information input may include one or more data objects. A data object may include information corresponding to a project questionnaire. The project questionnaire may include a plurality of data input fields. The data input fields may be provided to a user via a user interface. The user interface may be provided to the user via a suitable computing device, such as those described herein.

In some embodiments, the project questionnaire data input fields may be configured to allow the user to provide information corresponding to a respective project. In some embodiments, the data input fields may include drop down selection fields, radio button selection fields, free form text fields, other suitable data input fields, or a combination thereof. In some embodiments, the user may interact with the user interface to provide information (e.g., answers) corresponding to requests for information (e.g., questions) on the project questionnaire.

In some embodiments, the requests for information may include a plurality of request for information types. For example, the request for information types may include a time criticality request for information type, a business value request for information type, a risk reduction and opportunity enablement request for information type, an effort request for information type (e.g., indicating an effort associated with the respective project), any other suitable request for information type, or a combination thereof. A request for information type may be associated with one or more requests for information on the project questionnaire. For example, a first request for information type may corresponding to a plurality of requests for information. The first request for information type may correspond to the time criticality request for information type or other suitable request for information type. The plurality of requests for information may include a plurality of questions associated with time criticality of a corresponding project (e.g., "what does the time criticality curve look like?", "if he need by date is missed, is there value lost?", and the like).

In some embodiments, each of the requests for information of the project questionnaire includes an assigned weight value. Additionally, or alternatively, each of the requests for information having a pre-validated input (e.g., an input or response to a request for information that the user can select) may include an assigned score value. In some embodiments, the systems and methods described herein may be configured to determine a sum of all weighted score values for a request for information type. The systems and methods described herein may be configured to divide, for the respective request for information type, a corresponding weighted score value by a weight max value.

In some embodiments, the user may input information using the user interface to respond to the requests for information of the project questionnaire. The project questionnaire may be organized in multiple sections corresponding to the request for information types. For example, the project questionnaire may be organized into four sections each representing a respective request for information type (e.g., or other suitable number of sections). In some embodiments, the systems and methods described herein may be configured to determine a common value score for each respective project corresponding to a project questionnaire. For example, the systems and methods described herein may be configured to determine a sum of a first request for information type score (e.g., corresponding to a time criticality score), a first second request for information type score (e.g., corresponding to a business value score), and a third request for information type (e.g., corresponding to a risk reduction and opportunity enablement score). The systems and methods described herein may be configured to determine the common value score for the respective project by determining the result of the first sum by a fourth request for information type score (e.g., corresponding to an effort score).

In some embodiments, the systems and methods described herein may be configured to store the common value score for each respective project in a data store, such as a database (e.g., a standard query language database or other suitable data store). The systems and methods described herein may be configured to sort the common value scores for the respective projects in according to a sorting algorithm. For example, the systems and methods described herein may be configured to sort the common value scores in a descending order or other suitable order.

In some embodiments, the systems and methods described herein may be configured to generate one or more reports (e.g., which may be referred to as an opportunity canvas). For example, the systems and methods described herein may be configured to receive the common value scores from the data store. The systems and methods described herein may be configured to generate an output indicating the common value scores and/or any suitable information corresponding to each of the common value scores (e.g., project name, domain utilization, etc.). The systems and methods described herein may be configured to provide the output to a display, such as those described herein, and/or a file stored in a suitable memory.

In some embodiments, the systems and methods described herein may be configured to calibrate common value scoring based on feedback received from the user and/or other users. For example, the systems and methods described herein may be configured to revise various requests for information of the project questionnaire, revise various calculations, and the like based on the feedback.

In some embodiments, the systems and methods described herein may be configured to generate a data object, representing the information provided by the user in response to the requests for information on the project questionnaire, for a respective project. The data object may include any suitable data object and may follow any data object protocol or data structure. In some embodiments, the systems and methods described herein may be configured to identify information associated with one or more received data objects. For example, the systems and methods described herein may be configured to identify information corresponding to one or more requests for information of the project questionnaire.

In some embodiments, the information corresponding to the one or more requests for information represented in the one or more data objects may include numerical information (e.g., a first type of pre-validated input), fixed textual information (e.g., a second type of pre-validated input comprising one or more predefined text strings recognizable by the systems and methods described herein), free form textual information, other suitable information, or a combination thereof. The systems and methods described herein may be configured to recognize various aspects of the information corresponding to the one or more requests for information represented by the one or more data objects, such as numerical information, fixed textual information, and the like.

In some embodiment, the systems and methods described herein may be configured to identify information corresponding to the one or more requests for information that includes free form textual information using one or more natural language processing techniques. For example, the systems and methods described herein may be configured to process the free form textual information and generate output that represents the free form textual information. The systems and methods described herein may use the generated output to, at least, dynamically score the one or more projects represented by the one or more data objects. For example, the systems and methods described herein may be configured to identify one or more domains associated with a respective project represented by a corresponding data object.

In some embodiments, the systems and methods described herein may be configured to use an artificial intelligence engine that uses at least one machine learning model configured to perform natural language processing techniques. The systems and methods described herein may be configured to use the artificial intelligence engine to identify the information corresponding to the one or more requests for information that include free form textual information.

In some embodiments, the systems and methods described herein may be configured to receive a first data object, as described. It should be understood that the systems and methods described herein may be configured to receive any suitable number of data objects. The first data object may represent information corresponding to requests for information associated with a project questionnaire for a respective project. The first data object may indicate a first value associated with a first value type. The first value type may correspond to one of the request for information types, as described. The first value may correspond to information for a respective data input field on the project questionnaire. For example, the first value may correspond to information the user provided at the user interface in response to a request for information associated with the first value type.

In some embodiments, the first value may include a first weight value. The first data object may further indicate a second value associated with the first value type. The second value may correspond to information for another respective data input field on the project questionnaire. For example, the second value may correspond to information the user provided at the user interface in response to another request for information associated with the first value type (e.g., the project questionnaire may include multiple requests for information corresponding to a respective request for information type). The second value may include a second weight value.

In some embodiments, the first data object may further indicate a third value and a fourth value associated with a second value type. The third value may include a third weight value and the fourth value may include a fourth weight value. The first data object may further indicate a fifth value corresponding to a third value type. The third value type may correspond to an effort request for information type (e.g., indicating an amount of effort required for performing various aspects of the respective project).

In some embodiments, the systems and methods described herein may be configured to determine a first sum of a product of the first value and the first weight value plus a product of the second value and the second weight value. The systems and methods described herein may be configured to generate a first score based on a result of the first sum divided by a sum of the first weight value and the second weight value.

In some embodiments, the systems and methods described herein may be configured to determine a second sum of a product of the third value and the third weight value plus a product of the fourth value and the fourth weight value. The systems and methods described herein may be configured to generate a second score based on a result of the second sum divided by a sum of the third weight value and the fourth weight value.

In some embodiments, the first data object may further indicate a sixth value associated with a fourth value type and a seventh value associated with the fourth value type. The sixth value may include a fifth weight value and the seventh value may include a sixth weight value. The systems and methods described herein may be configured to determine a third sum of a product of the sixth value and the fifth weight value plus a product of the seventh value and the sixth weight value. The systems and methods described herein may be configured to generate a third score based on a result of the third sum divided by a sum of the fifth weight value and the sixth weight value.

In some embodiments, systems and methods described herein may be configured to determine a first data object score (e.g., a common value score for the project corresponding to the first data object) for the first data object based on the first score, the second score, the third score, and the fifth value. For example, the systems and methods described herein may be configured to determine a first sum of the first score, the second score, and the third score. The systems and methods described herein may be configured to generate the first data object score by determining the result of the first sum divided by the fifth value.

In some embodiments, the systems and methods described herein may be configured to generate a report comprising, at least, the first data object score and at least one other data object score. The first data object score and the at least one other data object may be organized on the report according to a dynamically generated order. In some embodiments, the systems and methods described herein may be configured to output, to a display, the report.

In some embodiments, the systems and methods described herein may be configured to perform evolutionary optimization to identify optimum or substantially optimum combinations of projects associated with data objects. The systems and methods described herein may be configured to use the common value scores for the respective data objects (e.g., corresponding to respective projects), domain costs corresponding to the respective data objects, or any other suitable information for the respective data objects to identify all possible combinations of data objects (which may be referred to as seeds). For example, the systems and methods described herein may be configured to generate a matrix of binary strings. Each binary string corresponds to a possible combination of data objects and includes a plurality of 1s and 0s. Each 1 in a binary string indicates that a corresponding data object is included in the binary string and each 0 in the binary string indicates that a corresponding data object is not included in the binary string.

In some embodiments, the systems and methods described herein may be configured to perform weight sort on a plurality of common value scores corresponding to respective ones of a plurality of data objects. The system and methods described herein may be configured to receive a depth value. The depth value may be provided by the user or other suitable user. In some embodiments, the depth value may be a predefined value or may be a value generated by the systems and methods described herein. The depth value may indicate a number of data objects in the plurality of data objects to consider when generated the possible combinations of data objects (e.g., the possible combinations of data objects may include all possible combinations of data objects indicated by the depth value).

The systems and methods described herein may be configured to identify data object combinations of the possible data object combinations having a value above a threshold. For example, the systems and methods described herein may be configured to determine a value realized for each data object combination of the possible data object combinations. As is generally illustrated in FIG. 4A, a first data object combination 402 may represent one data object combination of the possible data object combinations. As is generally illustrated, the data object combination 402 includes a depth value of 5 (e.g., considering 5 data objects). However, it should be understood that any suitable depth value may be used.

The data object 402 may be represented by a binary string, such as 01000. The binary string may represent which data objects are included in the data object combination 402. As is generally illustrated, data object 1 is not included in the data object combination 402, data object 2 is included in the data object combination 402, data object 3 is not included in the data object combination 402, data object 4 is not included in the data object combination 402, and data object 5 is not included in the data object combination 402. Each data object includes a value. For example, the data object 2 includes a value of $200. The value may represent a total benefit (e.g., tangible or intangible) expected from performing the project associated with the data object. Additionally, or alternatively, each data object includes a weight value. For example, the data object 2 includes a weight value of $3. The weight value may represent a total cost (e.g., tangle or intangible) associated with performing the project associated with the data object.

The data object combination 402 may include weight values associated with domains corresponding to the project associated with each data object. For example, the data object combination 402 may include a domain 1, a domain 2, and a domain 3. As described, a domain may represent a resource or group or resources required to perform the project associated with the data object. As is generally illustrated, the domain 1, the domain 2, and the domain 3 include a weight value of 1 for the data object 2. Correspondingly, the weight value for the data object 2 (e.g., and or any other data object) includes a sum of the weights of the domains. It should be understood that the values generally illustrated and described herein are for example purposes only and any suitable value may be used.

The systems and methods described herein may be configured to determine a total weight for a domain for the data object combination 402 by determining a sum of the domain weights for each data object included in the data object combination 402. For example, the data object 402 includes a total domain weight for domain 1 of $1 a total domain weight for domain 2 of $1, and a total domain weight for domain 3 of $1. Additionally, or alternatively, the systems and methods described herein may be configured to determine a total value realized for a data object combination. As is generally illustrated, the value realized for the data object combination 402 is $200.

As is generally illustrated in FIG. 4B, a data object 404 includes a binary string of 01011 (e.g., indicating that data object 2, data object 4, and data object 5 are included in the data object combination 404). The data object combination 404 includes a total domain weight for domain 1 of $1, a total domain weight for domain 2 of $4, and a total domain weight for domain 3 of $2. Additionally, or alternatively, the data object combination 404 includes a total value realized of $1,100.

In some embodiments, the systems and methods described herein may be configured to generate a first set of data object combinations based on total domain weight values for each of the possible data object combinations. For example, the systems and methods described herein may be configured to identify data object combinations having at least one total domain weight that is greater than threshold. The threshold may include a percentage (e.g., 95% or other suitable value) of a domain budget corresponding to the domain. If the systems and methods described herein identify a data object combination having a total domain weight value that is greater than the threshold, the systems and methods described herein discard the data object combination. That is, the systems and methods described herein may be configured to generate the first set of data object combinations using data object combinations having total domain weight values that are less than or equal to the threshold. As is generally illustrated, the systems and methods described herein may include the data object combination 402 and the data object combination 404 in the first set of data object combinations (e.g., because each of the total domain weight values is less than the threshold).

In some embodiments, the systems and methods described herein may be configured to generate a second set of data object combination using the first set of data object combinations. For example, the systems and methods described herein may be configured to determine a mutation rate value. The systems and methods described herein may be configured to receive the mutation rate value from the user or other suitable user, identify the mutation rate value stored in a suitable memory, generate a randomly determined mutation rate value, or determine the mutation rate value using any suitable technique. The mutation rate value may indicate a rate at which 1s and 0s of binary strings of randomly selected data object combinations of the first set of data object combinations are flipped (e.g., 1s changed to 0s and 0s changed to 1s).

The systems and methods described herein may be configured to apply the mutation rate value to the first set of data object combinations. For example, the systems and methods described herein may be configured to identify, at random, a number of data object combinations of the first set of data object combinations corresponding to the mutation rate value (e.g., a mutation rate value of 0.1 will result in the systems and methods described herein randomly selecting 10% of the data object combinations from the first set of data object combustions). The systems and methods described herein may be configured to flip is to 0s and 0s to 1s for binary strings corresponding to the selected data object combinations. The systems and methods described herein may be configured to generate the second set of data object combinations using the selected data object combinations (e.g., having is change to 0s and 0s changed to 1s for corresponding binary strings) and the other (e.g., 90%) data object combinations of the first set of data object combinations.

Figure 4C:
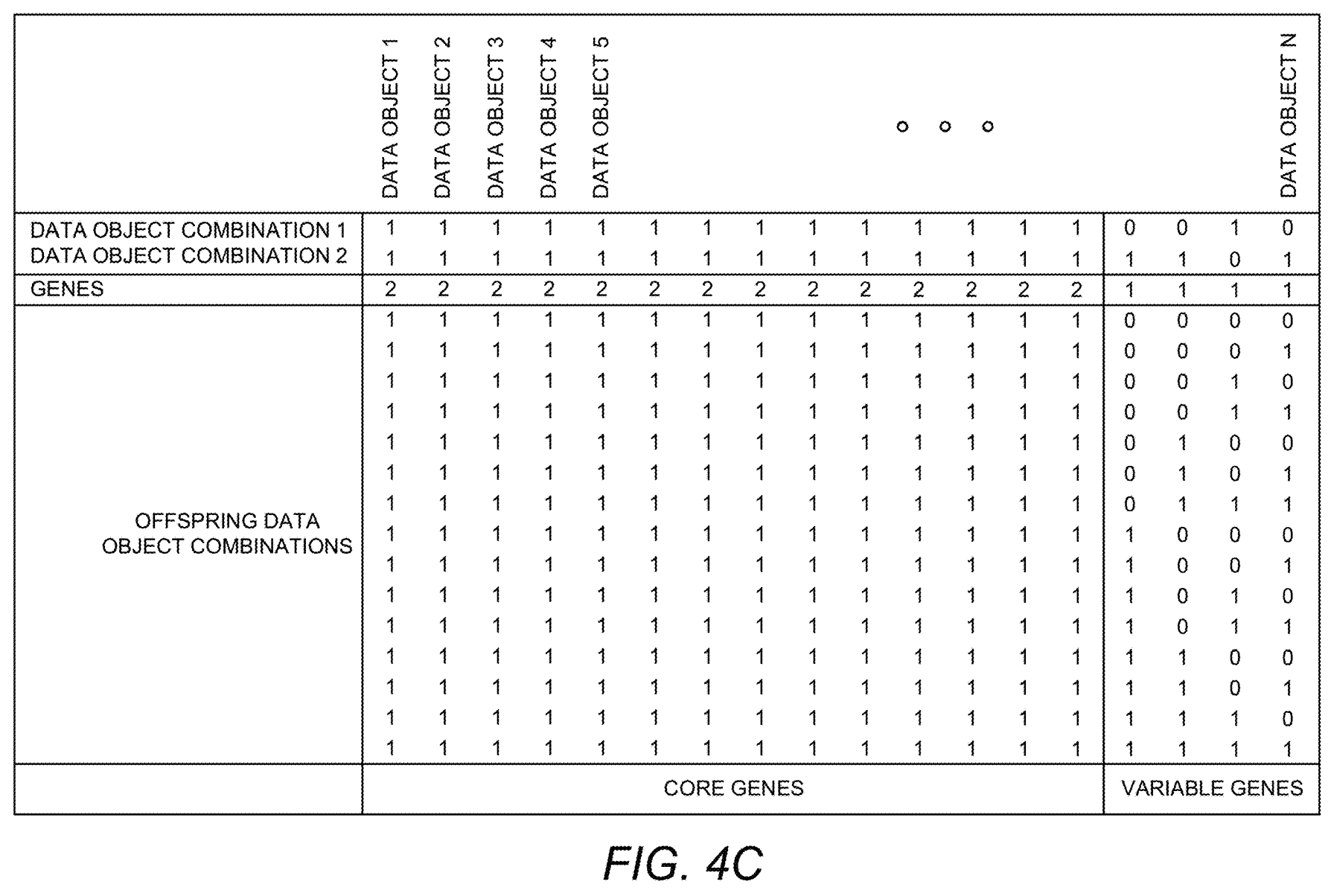

In some embodiments, the system and methods described herein may be configured to identify core data objects (e.g., which may be referred to as core genes) and variable data objects (e.g., which may be referred to as variable genes). For example, the systems and methods described herein may be configured to identify pairs of data object combinations from the second set of data object combinations. As is generally illustrated in FIG. 4C, the systems and methods described herein may identify a data object combination 1 and a data object combination 2. The systems and methods described herein may be configured to identify data objects included in both the data object combination 1 and the data object combination 2. For example, the systems and methods described herein may identify the data object 1, the data object 2, and so that are indicated as being included in both the data object combination 1 and the data object combination 2.

The systems and methods described herein may be configured to identify the data objects included in both the data object combination 1 and the data object combination 2 as core data objects. The systems and methods described herein may identify all other data objects (e.g., data objects included in only one of the data object combination 1 and the data object combination 2). The systems and methods described herein may be configured to generate offspring data combinations that include all possible data object combinations including all of the core data objects and every possible combination of variable data objects.

In some embodiments, the systems and methods described herein may iteratively identify, for a period corresponding to a search rate value, offspring data object combinations for other pairs of data object combinations from the second set of data object combinations. The search rate value may be provided by the user or other suitable user or retrieved from a suitable memory. The search rate value may indicate a length of time, a number of cycles, and the like that the systems and methods described herein may continue to identify offspring data combinations.

The systems and methods described herein may be configured to determine a total domain weight for each domain associated with each offspring data combination, as described. Additionally, or alternatively, the systems and methods described herein may be configured to determine a total value realized for each of the offspring data combinations.

In some embodiments, the systems and methods described herein may be configured to generate a third set of data object combinations based on the offspring data combinations. For example, the systems and methods described herein may be configured to identify offspring data combinations having at least one total domain weight value that is greater than the threshold, as described. The systems and methods described herein may disregard offspring data object combinations that included at least one total domain weight value that is greater than the threshold.

The systems and methods described herein may be configured to identify, of the offspring data object combinations not disregarded, offspring data object combinations having a total value realized greater than a highest total value realized in the previously identified data object combinations (e.g. for all data object combinations of the first set of data object combinations). The systems and method described herein may be configured to generate the third set of data object combinations using the offspring data object combinations not discarded that have a total value realized greater than the highest total value realized in the previously identified data object combinations.

The systems and methods described herein may continue to iteratively identify offspring data object combinations using the third set of data object combinations (e.g., and further generated sets of data object combinations) for a period corresponding to the search rate value or other suitable period. The systems and methods described herein may be configured to generate an output indicating a set of data object combinations corresponding to a final set of data object combinations identified by the systems and methods described herein. The final set of data object combinations may correspond to a set of optimal or substantially optimal data object combinations. The systems and methods described herein may be configured to provide the output, as described.

In some embodiments, the systems and methods described herein may be configured to receive a plurality of data objects. Each data object may include a corresponding score value and a corresponding weight value. The systems and methods described herein may be configured to determine, using natural language processing of the plurality of data objects, at least one resource domain. The at least one resource domain having a weight value and corresponding to resources utilized for a project associated with a corresponding data object of the plurality of data objects.

The systems and methods described herein may be configured to identify all possible data object combinations for at least some (e.g., according to the depth value) of the plurality of data objects for the at least one resource domain. Each data object combination may be represented by a binary data string indicating selected data objects for a respective data object combination. The systems and methods described herein may be configured to determine a total score value for each data object combination of the identified possible data object combinations by calculating a sum of the corresponding score values for each data object identified in a respective data object combination of the identified possible data object combinations.

The systems and methods described herein may be configured to determine a total weight value for each data object combination of the identified possible data object combinations by calculating a sum of the corresponding weight values for each data object identified in a respective data object combination of the identified possible data object combinations. The systems and methods described herein may be configured to identify data object combinations of the identified possible data object combinations having a total weight value less than or equal to the weight value of the at least one resource domain.

The systems and methods described herein may be configured to identify data object combinations, of the identified data object combinations of the possible data object combinations having a total weight value less than or equal to the weight value of the at least one resource domain, having a total score value greater than a first total score value threshold.

The systems and methods described herein may be configured to generate a first set of data object combinations using identified data object combinations, of the identified data object combinations of the possible data object combinations having a total weight value less than or equal to the weight value of the at least one resource domain, having a total score value greater than the first total score value threshold.

In some embodiments, the systems and methods described herein may be configured to determine a plurality of total values for each data object combination of the identified possible data object combinations. For example, the systems and methods described herein may determine a total compliance value for each data object combination, a total weight value for each data object combination, a total score value for each data object combination, a total technology score value for each data object combination, other suitable values for each data combination, or a combination thereof.

In some embodiments, the systems and methods described herein may be configured to a benefit for each data object combination based on a theme corresponding to one or more of the plurality of total values. The theme may include a technology them, a compliance theme, a monetary theme, and the like. The theme may include a threshold value corresponding to a subject matter of the theme. For example, a technology theme may include a theme threshold of 40% (e.g., indicating that data object combinations at least 40% of corresponding data objects directed to technology projects are equal to or above the threshold). The systems and methods described herein may identify data object combinations having a theme value greater than the threshold. For example, the systems and methods described herein may use one or more of the plurality of total values to identify data object combinations having a total theme score that is greater than or equal to the threshold.

In some embodiments, the systems and methods described herein may identify data object combinations of the identified data object combinations (e.g., having a total theme score greater than or equal to the theme threshold), having a total value score greater than or equal to a value threshold. For example, the systems and methods described herein may be configured to identify data object combinations having at least 40% of corresponding data objects directed to technology projects and having a total value score that is greater than or equal to a monetary value threshold. It should be understood that the systems and methods described herein may be configured to identify the data object combinations using any suitable theme, value, information, and the like.

In some embodiments, the systems and methods described herein may be configured to set a mutation variable to a predetermine value. The systems and methods described herein may be configured to apply the mutation variable to the first set of data object combinations. The systems and methods described herein may be configured to select at least two data object combinations of the first set of data object combinations after application of the mutation variable to the first set of data object combinations.

In some embodiments, the systems and methods described herein may be configured to identify data objects that appear in each of the at least two data object combinations of the first set of data object combinations. In some embodiments, the at least two data object combinations may be identified at random, may be identified based on a reward function of weight objectives, identified based on one or more of the plurality of total values, identified using other suitable information, or a combination thereof. The systems and methods described herein may be configured to generate, using an artificial intelligence engine configured to use at least one machine learning model configured to identify data object combinations, a second set of data object combinations using the data objects that appear in each of the at least two data object combinations of the first set of data object combinations and each possible combination of data objects that do not appear in at least one data object combination of the at least two data object combinations of the first set of data object combinations.

In some embodiments, the systems and methods described herein may be configured to provide, to a display, output indicating data object combinations of the second set of data object combinations having a total score value above a second total score value threshold.

FIG. 1A is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
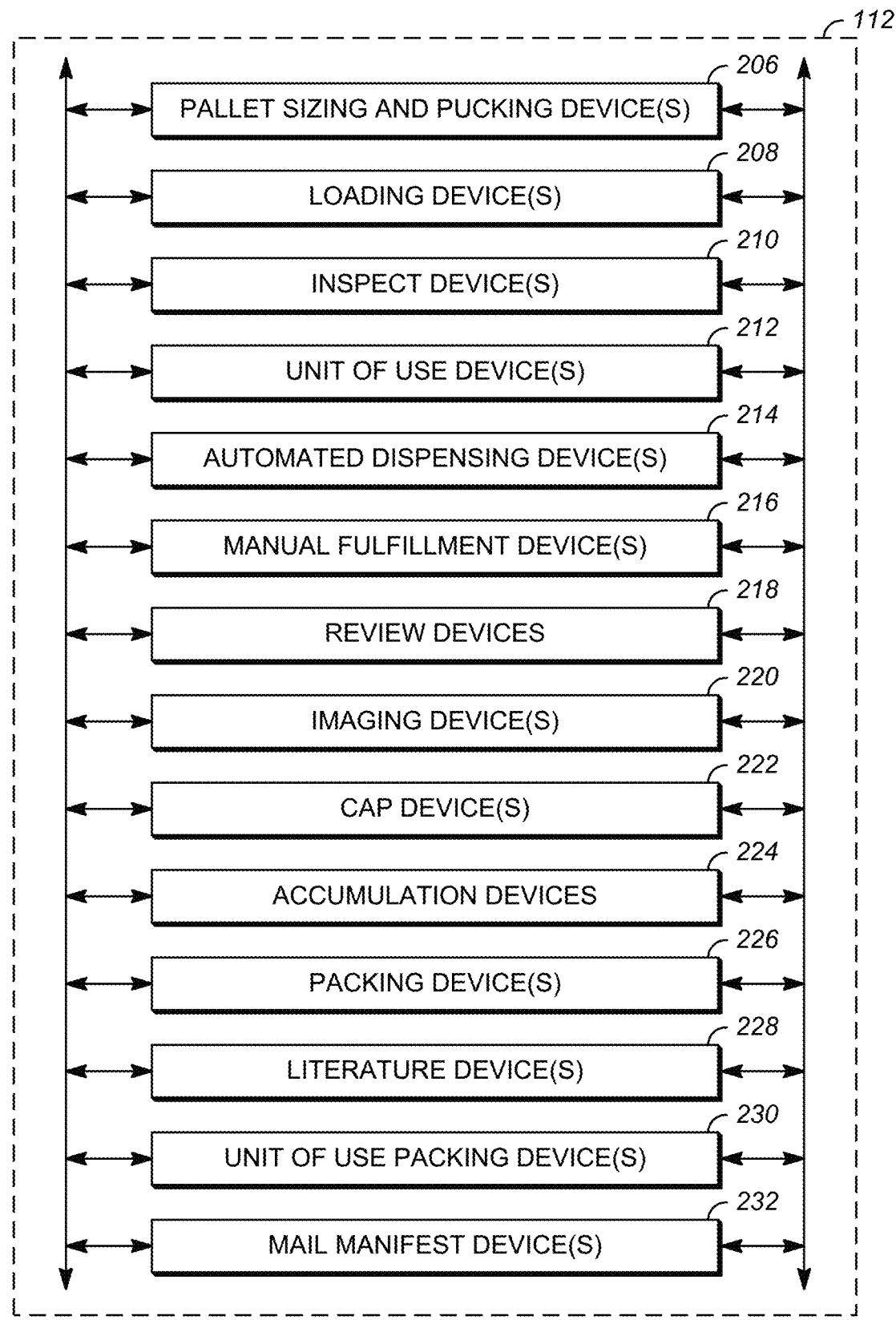
FIG. 2 generally illustrates a functional block diagram of a pharmacy fulfillment device, which may be deployed within the system of FIG. 1A.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
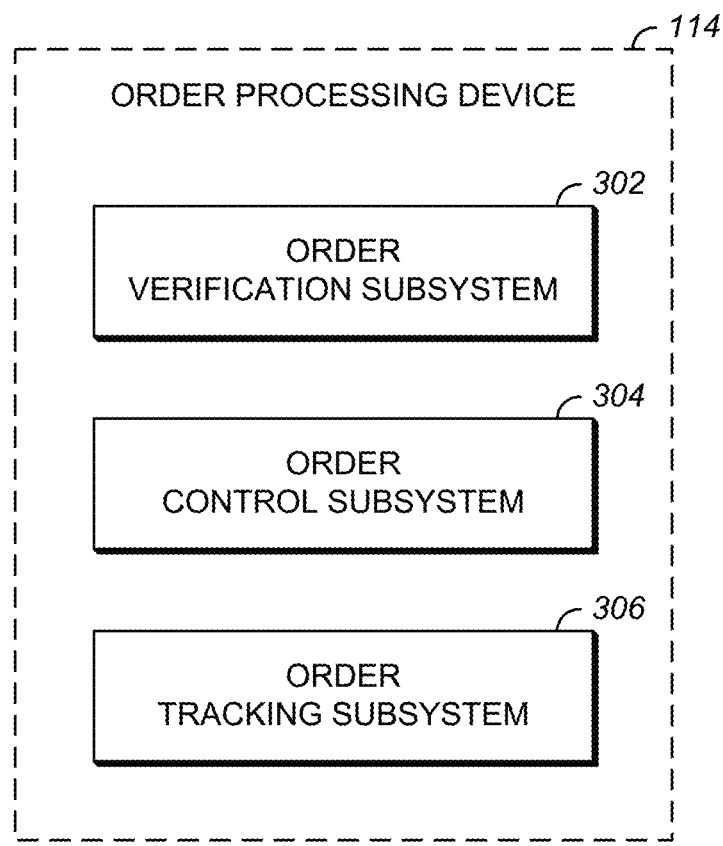
FIG. 3 generally illustrates a functional block diagram of an order processing device, which may be deployed within the system of FIG. 1A.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Figure 1B:
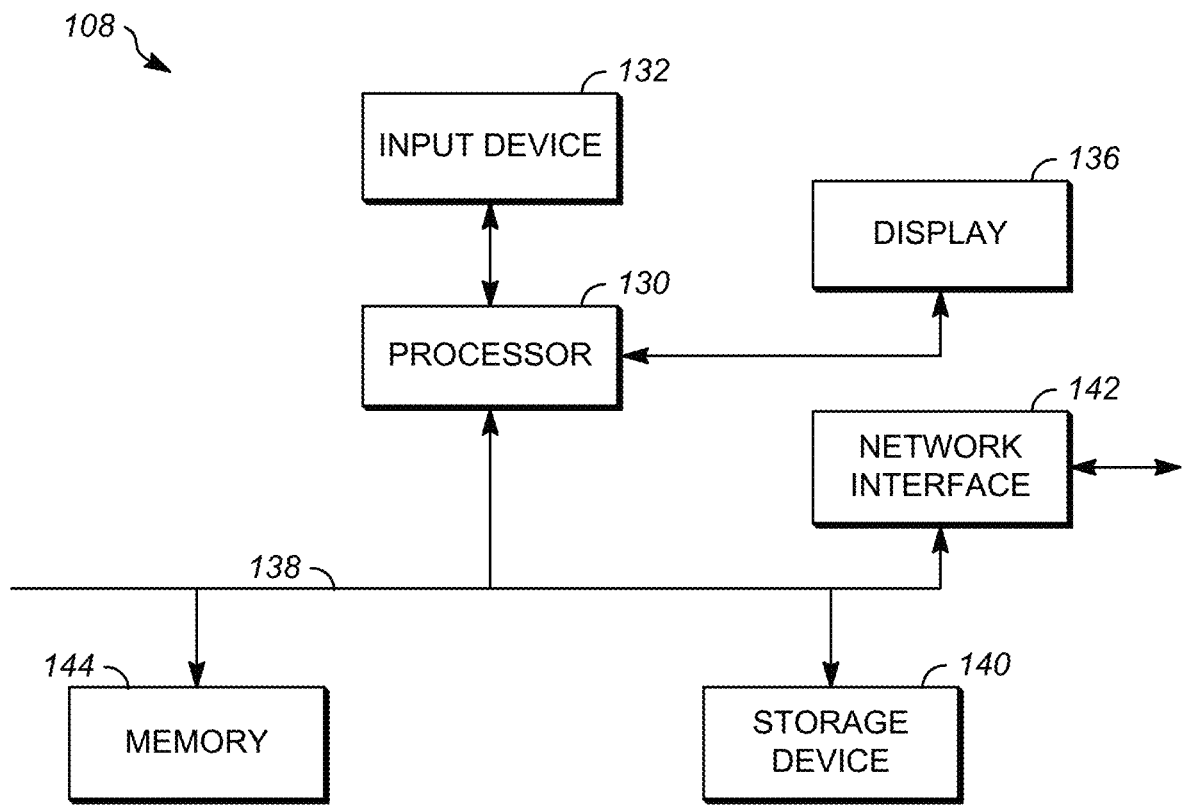

In some embodiments, the system 100 may include one or more computing devices 108, as is generally illustrated in FIG. 1B. The computing device 108 may include any suitable computing device, such as a mobile computing device, a desktop computing device, a laptop computing device, a server computing device, other suitable computing device, or a combination thereof. The computing device 108 may be used by a user accessing the pharmacy associated with the system 100, as described. Additionally, or alternatively, the computing device 108 may be configured to identify an optimum or substantially optimum combination of data objects, as described.

The computing device 108 may include a processor 130 configured to control the overall operation of computing device 108. The processor 130 may include any suitable processor, such as those described herein. The computing device 108 may also include a user input device 132 that is configured to receive input from a user of the computing device 108 and to communicate signals representing the input received from the user to the processor 130. For example, the user input device 132 may include a button, keypad, dial, touch screen, audio input interface, visual/image capture input interface, input in the form of sensor data, etc.

The computing device 108 may include a display 136 that may be controlled by the processor 130 to display information to the user. A data bus 138 may be configured to facilitate data transfer between, at least, a storage device 140 and the processor 130. The computing device 108 may also include a network interface 142 configured to couple or connect the computing device 108 to various other computing devices or network devices via a network connection, such as a wired or wireless connection, such as the network 104. In some embodiments, the network interface 142 includes a wireless transceiver.

The storage device 140 may comprise a single disk or a plurality of disks (e.g., hard drives), one or more solid-state drives, one or more hybrid hard drives, and the like. The storage device 140 may include a storage management module that manages one or more partitions within the storage device 140. In some embodiments, storage device 140 may include flash memory, semiconductor (solid state) memory or the like. The computing device 108 may also include a memory 144. The memory 144 may include Random Access Memory (RAM), a Read-Only Memory (ROM), or a combination thereof. The memory 144 may store programs, utilities, or processes to be executed in by the processor 130. The memory 144 may provide volatile data storage, and stores instructions related to the operation of the computing device 108.

In some embodiments, the processor 130 may be configured to execute instructions stored on the memory 144 to, at least, perform the systems and methods described herein. In some embodiments, the computing device 108 may be configured to receive a first data object, as described. It should be understood that the computing device 108 may receive any suitable number of data objects. The first data object may represent information corresponding to requests for information associated with a project questionnaire for a respective project. The first data object may indicate a first value associated with a first value type. The first value type may correspond to one of the request for information types, as described. The first value may correspond to information for a respective data input field on the project questionnaire. For example, the first value may correspond to information the user provided at the user interface in response to a request for information associated with the first value type.

In some embodiments, the first value may include a first weight value. The first data object may further indicate a second value associated with the first value type. The second value may correspond to information for another respective data input field on the project questionnaire. For example, the second value may correspond to information the user provided at the user interface in response to another request for information associated with the first value type (e.g., the project questionnaire may include multiple requests for information corresponding to a respective request for information type). The second value may include a second weight value.

In some embodiments, the first data object may further indicate a third value and a fourth value associated with a second value type. The third value may include a third weight value and the fourth value may include a fourth weight value. The first data object may further indicate a fifth value corresponding to a third value type. The third value type may correspond to an effort request for information type (e.g., indicating an amount of effort required for performing various aspects of the respective project).

In some embodiments, the computing device 108 may determine a first sum of a product of the first value and the first weight value plus a product of the second value and the second weight value. The computing device 108 may generate a first score based on a result of the first sum divided by a sum of the first weight value and the second weight value.

In some embodiments, the computing device 108 may determine a second sum of a product of the third value and the third weight value plus a product of the fourth value and the fourth weight value. The computing device 108 may generate a second score based on a result of the second sum divided by a sum of the third weight value and the fourth weight value.

In some embodiments, the first data object may further indicate a sixth value associated with a fourth value type and a seventh value associated with the fourth value type. The sixth value may include a fifth weight value and the seventh value may include a sixth weight value. The computing device 108 may determine a third sum of a product of the sixth value and the fifth weight value plus a product of the seventh value and the sixth weight value. The computing device 108 may generate a third score based on a result of the third sum divided by a sum of the fifth weight value and the sixth weight value.

In some embodiments, computing device 108 may determine a first data object score (e.g., a common value score for the project corresponding to the first data object) for the first data object based on the first score, the second score, the third score, and the fifth value. For example, the computing device 108 may determine a first sum of the first score, the second score, and the third score. The computing device 108 may generate the first data object score by determining the result of the first sum divided by the fifth value.

In some embodiments, the computing device 108 may generate a report comprising, at least, the first data object score and at least one other data object score. The first data object score and the at least one other data object may be organized on the report according to a dynamically generated order. In some embodiments, the computing device 108 may output, to a display, such as the display 136 or other suitable display, the report.

In some embodiments, the computing device 108 may receive a plurality of data objects. Each data object may include a corresponding score value and a corresponding weight value. The computing device 108 may determine, using natural language processing of the plurality of data objects, at least one resource domain. The at least one resource domain having a weight value and corresponding to resources utilized for a project associated with a corresponding data object of the plurality of data objects.

The computing device 108 may identify all possible data object combinations for at least some (e.g., according to the depth value) of the plurality of data objects for the at least one resource domain. Each data object combination may be represented by a binary data string indicating selected data objects for a respective data object combination. The computing device 108 may determine a total score value for each data object combination of the identified possible data object combinations by calculating a sum of the corresponding score values for each data object identified in a respective data object combination of the identified possible data object combinations.

The computing device 108 may determine a total weight value for each data object combination of the identified possible data object combinations by calculating a sum of the corresponding weight values for each data object identified in a respective data object combination of the identified possible data object combinations. The computing device 108 may identify data object combinations of the identified possible data object combinations having a total weight value less than or equal to the weight value of the at least one resource domain.

The computing device 108 may identify data object combinations, of the identified data object combinations of the possible data object combinations having a total weight value less than or equal to the weight value of the at least one resource domain, having a total score value greater than a first total score value threshold.

The computing device 108 may generate a first set of data object combinations using identified data object combinations, of the identified data object combinations of the possible data object combinations having a total weight value less than or equal to the weight value of the at least one resource domain, having a total score value greater than the first total score value threshold.

In some embodiments, the computing device 108 may set a mutation variable to a predetermine value. The computing device 108 may apply the mutation variable to the first set of data object combinations. The computing device 108 may select at least two data object combinations of the first set of data object combinations after application of the mutation variable to the first set of data object combinations.

In some embodiments, the computing device 108 may identify data objects that appear in each of the at least two data object combinations of the first set of data object combinations. The computing device 108 may generate, using an artificial intelligence engine configured to use at least one machine learning model configured to identify data object combinations, a second set of data object combinations using the data objects that appear in each of the at least two data object combinations of the first set of data object combinations and each possible combination of data objects that do not appear in at least one data object combination of the at least two data object combinations of the first set of data object combinations.

The artificial intelligence engine may use one or more machine learning models to perform at least one of the embodiments disclosed herein. The computing device 108 may include a training engine capable of generating the one or more machine learning models. The machine learning models may be trained to identify natural language (e.g., human language) provided by the user in response to requests for information on the project questionnaire, to identify domains associated with data objects, and/or to iteratively identify data object combinations, as described.

The one or more machine learning models may be generated by the training engine and may be implemented in computer instructions executable by one or more processing devices of the computing device 108. To generate the one or more machine learning models, the training engine may train the one or more machine learning models using feedback provided by the user (e.g., as described) or generated by the computing device 108.

In some embodiments, the computing device 108 may provide, to a display, such as the display 136 or other suitable display, output indicating data object combinations of the second set of data object combinations having a total score value above a second total score value threshold.

In some embodiments, the computing device 108 and/or the system 100 may perform the methods described herein. However, the methods described herein as performed by the computing device 108 and/or the system 100 are not meant to be limiting, and any type of software executed on a computing device or a combination of various computing devices can perform the methods described herein without departing from the scope of this disclosure.

Figure 5:
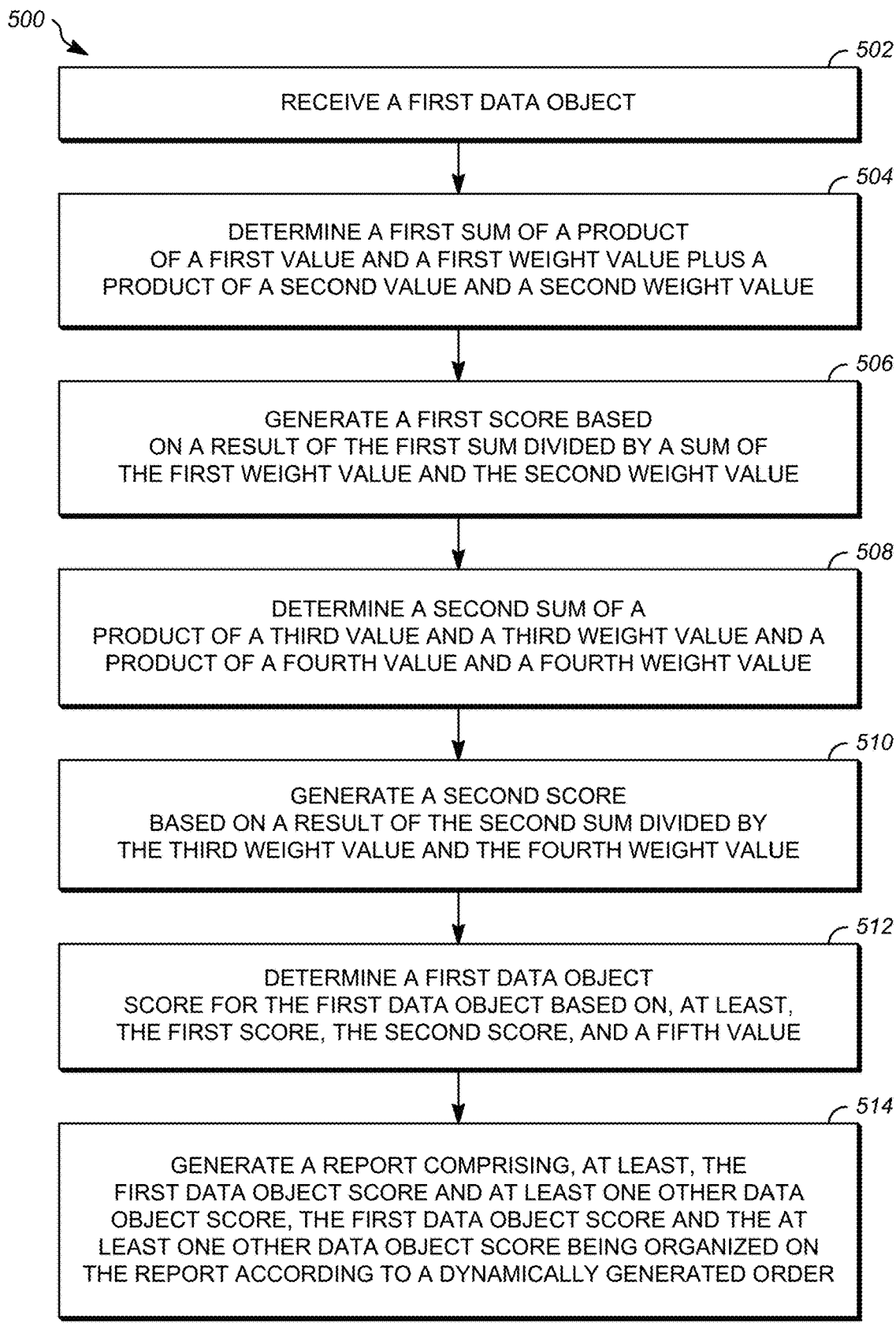
FIG. 5 is a flow diagram generally illustrating a dynamic data object scoring method according to the principles of the present disclosure.

FIG. 5 is a flow diagram generally illustrating a dynamic data object scoring method 500 according to the principles of the present disclosure. At 502, the method 500 receives a first data object indicating. For example, the computing device 108 may receive the first data object. The first data object may indicate a first value associated with a first value type. The first value may include a first weight value. The first data object may further indicate a second value associated with the first value type. The second value may include a second weight value. The first data object may further indicate a third value associated with a second value type. The third value may include a third weight value. The first data object may further indicate a fourth value associated with the second value type. The fourth value may include a fourth weight value. The first data object may further indicate a fifth value corresponding to a third value type.

At 504, the method 500 may determine a first sum of a product of the first value and the first weight value plus a product of the second value and the second weight value. For example, the computing device 108 may determine the first sum of the product of the first value and the first weight value plus the product of the second value and the second weight value.

At 506, the method 500 generates a first score based on a result of the first sum divided by a sum of the first weight value and the second weight value. For example, the computing device 108 may generate the first score based on the result of the first sum divided by the sum of the first weight value and the second weight value.

At 508, the method 500 determines a second sum of a product of the third value and the third weight value plus a product of the fourth value and the fourth weight value. For example, the computing device 108 may determine the second sum of the product of the third value and the third weight value plus the product of the fourth value and the fourth weight value.

At 510, the method 500 generates a second score based on a result of the second sum divided by a sum of the third weight value and the fourth weight value. For example, the computing device 108 may generate the second score based on the result of the second sum divided by the sum of the third weight value and the fourth weight value.

At 512, the method 500 determines a first data object score for the first data object based on, at least, the first score, the second score, and the fifth value. For example, the computing device 108 may determine the first data object score for the first data object based on, at least, the first score, the second score, and the fifth value.

At 514, the method 500 generates a report comprising, at least, the first data object score and at least one other data object score, the first data object score and the at least one other data object score being organized on the report according to a dynamically generated order. For example, the computing device 108 may generate the report comprising, at least, the first data object score and at least one other data object score, the first data object score and the at least one other data object score being organized on the report according to a dynamically generated order.

Figure 6A:
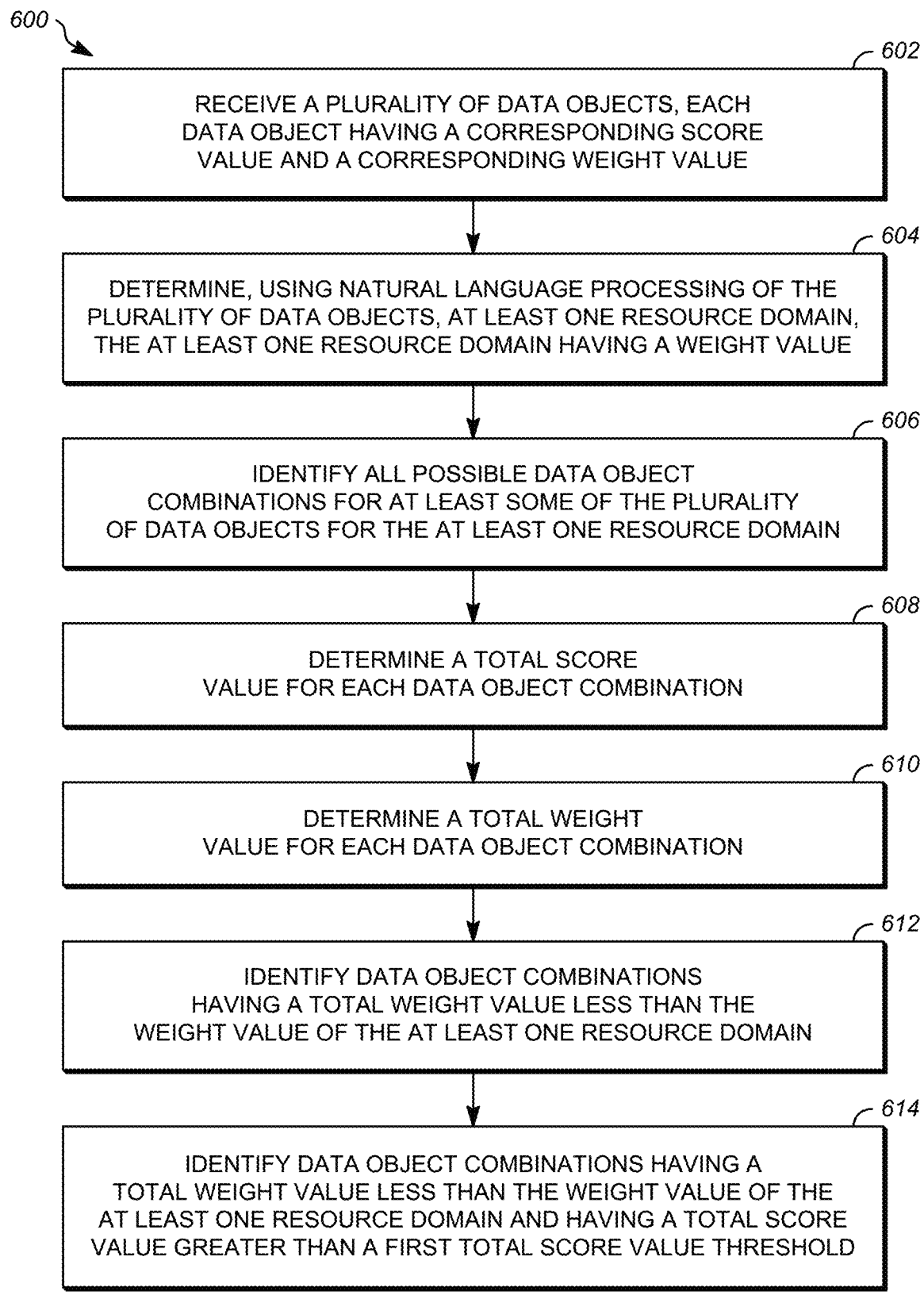
FIGS. 6A and 6B is a flow diagram generally illustrating a data object evolutionary optimization method according to the principles of the present disclosure.
Figure 6B:
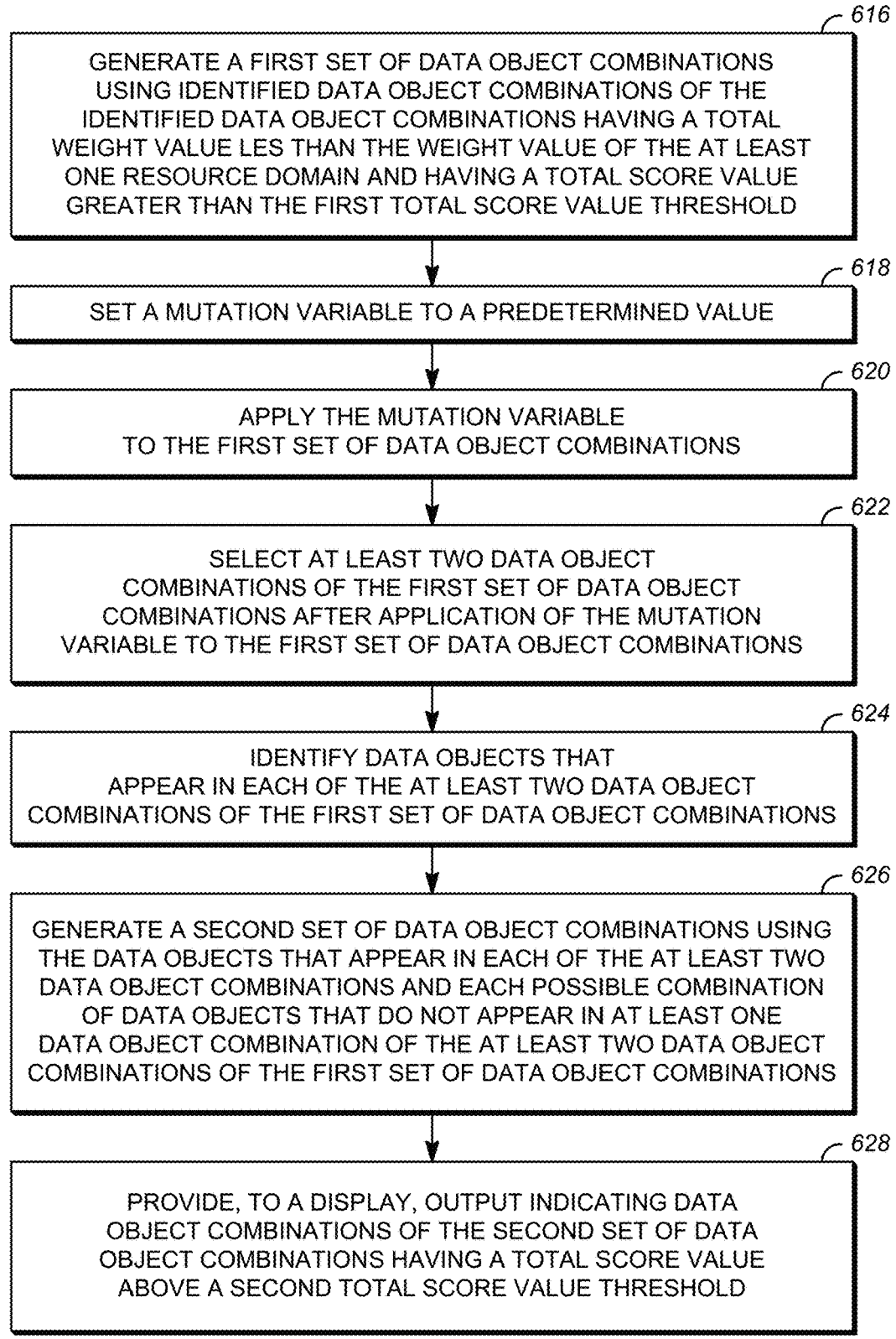

FIGS. 6A and 6B is a flow diagram generally illustrating a data object evolutionary optimization method 600 according to the principles of the present disclosure. At 602, the method 600 receives a plurality of data objects, each data object having a corresponding score value and a corresponding weight value. For example, the computing device 108 may receive the plurality of data objects.

At 604, the method 600 determines, using natural language processing of the plurality of data objects, at least one resource domain, the at least one resource domain having a weight value. For example, the computing device 108 may determine, using natural language processing of the plurality of data objects, the at least one resource domain.

At 606, the method 600 identifies all possible data object combinations for at least some of the plurality of data objects for the at least one resource domain. For example, the computing device 108 may identify all possible data object combinations for at least some of the plurality of data objects for the at least one resource domain. Each data object combination may be represented by a binary data string indicating selected data objects for a respective data object combination.

At 608, the method 600 determines a total score value for each data object combination. For example, the computing device 108 may determine the total score value for each data object combination of the identified possible data object combinations by calculating a sum of the corresponding score values for each data object identified in a respective data object combination of the identified possible data object combinations.

At 610, the method 600 may determine a total weight value for each data object combination. For example, the computing device 108 may determine the total weight value for each data object combination of the identified possible data object combinations by calculating a sum of the corresponding weight values for each data object identified in a respective data object combination of the identified possible data object combinations.

At 612, the method 600 identifies data object combinations having a total weight value less than or equal to the weight value of the at least one resource domain and having a total score value greater than a first total score value threshold. For example, the computing device 108 may identify the data object combinations of the identified possible data object combinations having a total weight value less than or equal to the weight value of the at least one resource domain. The computing device 108 may identify data object combinations, of the identified data object combinations of the possible data object combinations having a total weight value less than or equal to the weight value of the at least one resource domain, having a total score value greater than a first total score value threshold.

At 616, the method 600 generates a first set of data object combinations using identified data object combinations, of the identified data object combinations of the possible data object combinations having a total weight value less than or equal to the weight value of the at least one resource domain, having a total score value greater than the first total score value threshold. For example, the computing device 108 may generate the first set of data object combinations using identified data object combinations, of the identified data object combinations of the possible data object combinations having a total weight value less than or equal to the weight value of the at least one resource domain, having a total score value greater than the first total score value threshold At 618, the method 600 sets a mutation variable to a predetermined value. For example, the computing device 108 may set the mutation variable to the predetermine value.

At 620, the method 600 applies the mutation variable to the first set of data object combinations. For example, the computing device 108 may apply the mutation variable to the first set of data object combinations.

At 622, the method 600 selects at least two data object combinations of the first set of data object combinations after application of the mutation variable to the first set of data object combinations. For example, the computing device 108 may select the at least two data object combinations of the first set of data object combinations after application of the mutation variable to the first set of data object combinations.

At 624, the method 600 identifies data objects that appear in each of the at least two data object combinations of the first set of data object combinations. For example, the computing device 108 may identify the data objects that appear in each of the at least two data object combinations of the first set of data object combinations.

At 626, the method 600 generates, using an artificial intelligence engine configured to use at least one machine learning model configured to identify data object combinations, a second set of data object combinations using the data objects that appear in each of the at least two data object combinations of the first set of data object combinations and each possible combination of data objects that do not appear in at least one data object combination of the at least two data object combinations of the first set of data object combinations. For example, the computing device 108 may generate, using the artificial intelligence engine (e.g., configured to use the at least one machine learning model configured to identify data object combinations), the second set of data object combinations using the data objects that appear in each of the at least two data object combinations of the first set of data object combinations and each possible combination of data objects that do not appear in at least one data object combination of the at least two data object combinations of the first set of data object combinations.

At 628, the method 600 provides, to a display, output indicating data object combinations of the second set of data object combinations having a total score value above a second total score value threshold. For example, the computing device 108 may provide, to a display, such as the display 136 or other suitable display, output indicating the data object combinations of the second set of data object combinations having a total score value above a second total score value threshold In some embodiments, a system for dynamically scoring aspects of a data object includes a processor and a memory. The memory includes instructions that, when executed by the processor, cause the processor to: receive a first data object indicating: a first value associated with a first value type, the first value corresponding to a first weight value; a second value associated with the first value type, the second value corresponding to a second weight value; a third value associated with a second value type, the third value corresponding to a third weight value; a fourth value associated with the second value type, the fourth value corresponding to a fourth weight value; and a fifth value corresponding to a third value type; determine a first sum of a product of the first value and the first weight value plus a product of the second value and the second weight value; generate a first score based on a result of the first sum divided by a sum of the first weight value and the second weight value; determine a second sum of a product of the third value and the third weight value plus a product of the fourth value and the fourth weight value; generate a second score based on a result of the second sum divided by a sum of the third weight value and the fourth weight value; and determine a first data object score for the first data object based on, at least, the first score, the second score, and the fifth value.

In some embodiments, the first data object further indicates a sixth value associated with a fourth value type and a seventh value associated with the fourth value type, the sixth value corresponding to a fifth weight value and the seventh value corresponding to a sixth weight value. In some embodiments, the instructions further cause the processor to: determine a third sum of a product of the sixth value and the fifth weight value plus a product of the seventh value and the sixth weight value; and generate a third score based on a result of the third sum divided by a sum of the fifth weight value and the sixth weight value. In some embodiments, the instructions further cause the processor to determine the first data object score further based on the third score. In some embodiments, the first score corresponds to one of a business valuation and a time criticality. In some embodiments, the second score corresponds to the other of the business valuation and the time criticality. In some embodiments, the fifth value corresponds to an amount of effort associated with execution of a project associated with the first data object. In some embodiments, the instructions further cause the processor to generate a report comprising, at least, the first data object score and at least one other data object score, wherein the first data object score and the at least one other data object are organized on the report according to a dynamically generated order. In some embodiments, the instructions further cause the processor to output, to a display, the report.

In some embodiments, a method for dynamically scoring aspects of a data object includes receiving a first data object indicating: a first value associated with a first value type, the first value corresponding to a first weight value; a second value associated with the first value type, the second value corresponding to a second weight value; a third value associated with a second value type, the third value corresponding to a third weight value; a fourth value associated with the second value type, the fourth value corresponding to a fourth weight value; and a fifth value corresponding to a third value type. The method also includes determining a first sum of a product of the first value and the first weight value plus a product of the second value and the second weight value and generating a first score based on a result of the first sum divided by a sum of the first weight value and the second weight value. The method also includes determining a second sum of a product of the third value and the third weight value plus a product of the fourth value and the fourth weight value and generating a second score based on a result of the second sum divided by a sum of the third weight value and the fourth weight value. The method also includes determining a first data object score for the first data object based on, at least, the first score, the second score, and the fifth value.

In some embodiments, the first data object further indicates a sixth value associated with a fourth value type and a seventh value associated with the fourth value type, the sixth value corresponding to a fifth weight value and the seventh value corresponding to a sixth weight value. In some embodiments, the method also includes: determining a third sum of a product of the sixth value and the fifth weight value plus a product of the seventh value and the sixth weight value; and generating a third score based on a result of the third sum divided by a sum of the fifth weight value and the sixth weight value. In some embodiments, the method also includes determining the first data object score further based on the third score. In some embodiments, the first score corresponds to one of a business valuation and a time criticality. In some embodiments, the second score corresponds to the other of the business valuation and the time criticality. In some embodiments, the fifth value corresponds to an amount of effort associated with execution of a project associated with the first data object. In some embodiments, the method also includes generating a report comprising, at least, the first data object score and at least one other data object score, wherein the first data object score and the at least one other data object are organized on the report according to a dynamically generated order. In some embodiments, the method also includes outputting, to a display, the report.

In some embodiments an apparatus for dynamically scoring aspects of a data object includes a processor and a memory. The memory includes instructions that, when executed by the processor, cause the processor to: receive a first data object indicating: a first value associated with a first value type, the first value corresponding to a first weight value; a second value associated with the first value type, the second value corresponding to a second weight value; a third value associated with a second value type, the third value corresponding to a third weight value; a fourth value associated with the second value type, the fourth value corresponding to a fourth weight value; and a fifth value corresponding to a third value type, the fifth value corresponding to an amount of effort associated with execution of a project associated with the first data object; determine a first sum of a product of the first value and the first weight value plus a product of the second value and the second weight value; generate a first score based on a result of the first sum divided by a sum of the first weight value and the second weight value; determine a second sum of a product of the third value and the third weight value plus a product of the fourth value and the fourth weight value; generate a second score based on a result of the second sum divided by a sum of the third weight value and the fourth weight value; determine a first data object score for the first data object based on, at least, the first score, the second score, and the fifth value; and generate a report comprising, at least, the first data object score and at least one other data object score, wherein the first data object score and the at least one other data object are organized on the report according to a dynamically generated order.

In some embodiments, the instructions further cause the processor to output, to a display, the report.

In some embodiments, an evolutionary optimization system includes a processor and a memory. The memory includes instructions that, when executed by the processor, cause the processor to: receive a plurality of data objects, each data object having a corresponding score value and a corresponding weight value; identify all possible data object combinations for at least some of the plurality of data objects, each data object combination being represented by a binary data string; determine a total score value for each data object combination of the identified possible data object combinations by calculating a sum of the corresponding score values for each data object identified in a respective data object combination of the identified possible data object combinations; generate a first set of data object combinations using the total score value for each data object combination of the identified possible data object combinations and at least a total weight value for each data object combination of the identified possible data object combinations; set a mutation variable to a predetermine value; apply the mutation variable to the first set of data object combinations; select at least two data object combinations of the first set of data object combinations after application of the mutation variable to the first set of data object combinations; identify data objects that appear in each of the at least two data object combinations of the first set of data object combinations; and generate a second set of data object combinations using the data objects that appear in each of the at least two data object combinations of the first set of data object combinations and each possible combination of data objects that do not appear in at least one data object combination of the at least two data object combinations of the first set of data object combinations.

In some embodiments, the at least some of the plurality of data objects used to identify all possible data object combinations corresponds to a predetermined data object list depth. In some embodiments, the instructions further cause the processor to determine a total score value for each data object combination of the second set of data object combinations by calculating a sum of the corresponding score values for each data object identified in a respective data object combination of the second set of data object combinations. In some embodiments, the instructions further cause the processor to identify a third set of data object combinations that includes data object combinations of the second set of data object combinations having a total score value above a threshold total score value and a at least a total weight value for each data object combination of the second set of data object combinations. In some embodiments, the threshold total score value includes a highest total score value of the data object combinations of the first set of data object combinations. In some embodiments, a score value for a respective data object corresponds to a positive benefit derived from the respective data object. In some embodiments, a weight value for a respective data object corresponds to a cost derived from the respective data object. In some embodiments, the instructions further cause the processor to generate the second set of data object combinations using an artificial intelligence engine configured to use at least one machine learning model trained to identify data object combinations. In some embodiments, the at least one machine learning model is initially trained using a plurality of previously identified data object combinations. In some embodiments, the at least one machine learning model is iteratively trained using at least output of the at least one machine learning model. In some embodiments, each data object combination corresponds to a resource domain and wherein the instructions further cause the processor to identify resource domains for each data object combination using natural language processing.

In some embodiments, a method for providing evolutionary optimization includes receiving a plurality of data objects, each data object having a corresponding score value and a corresponding weight value and identifying all possible data object combinations for at least some of the plurality of data objects, each data object combination being represented by a binary data string. The method also includes determining a total score value for each data object combination of the identified possible data object combinations by calculating a sum of the corresponding score values for each data object identified in a respective data object combination of the identified possible data object combinations and generating a first set of data object combinations using the total score value for each data object combination of the identified possible data object combinations and at least a total weight value for each data object combination of the identified possible data object combinations. The method also includes setting a mutation variable to a predetermine value and applying the mutation variable to the first set of data object combinations. The method also includes selecting at least two data object combinations of the first set of data object combinations after application of the mutation variable to the first set of data object combinations and identifying data objects that appear in each of the at least two data object combinations of the first set of data object combinations. The method also includes generating a second set of data object combinations using the data objects that appear in each of the at least two data object combinations of the first set of data object combinations and each possible combination of data objects that do not appear in at least one data object combination of the at least two data object combinations of the first set of data object combinations.

In some embodiments, the at least some of the plurality of data objects used to identify all possible data object combinations corresponds to a predetermined data object list depth. In some embodiments, the method also includes determining a total score value for each data object combination of the second set of data object combinations by calculating a sum of the corresponding score values for each data object identified in a respective data object combination of the second set of data object combinations. In some embodiments, the method also includes identifying a third set of data object combinations that includes data object combinations of the second set of data object combinations having a total score value above a threshold total score value and a at least a total weight value for each data object combination of the second set of data object combinations. In some embodiments, the threshold total score value includes a highest total score value of the data object combinations of the first set of data object combinations. In some embodiments, a score value for a respective data object corresponds to a positive benefit derived from the respective data object. In some embodiments, a weight value for a respective data object corresponds to a cost derived from the respective data object. In some embodiments, the method also includes generating the second set of data object combinations using an artificial intelligence engine configured to use at least one machine learning model trained to identify data object combinations.

In some embodiments, an evolutionary optimization apparatus includes a processor and a memory that includes instructions that, when executed by the processor, cause the processor to: receive a plurality of data objects, each data object having a corresponding score value and a corresponding weight value; determine, using natural language processing of the plurality of data objects, at least one resource domain, the at least one resource domain having a weight value; identify all possible data object combinations for at least some of the plurality of data objects for the at least one resource domain, each data object combination being represented by a binary data string indicating selected data objects for a respective data object combination; determine a total score value for each data object combination of the identified possible data object combinations by calculating a sum of the corresponding score values for each data object identified in a respective data object combination of the identified possible data object combinations; determine a total weight value for each data object combination of the identified possible data object combinations by calculating a sum of the corresponding weight values for each data object identified in a respective data object combination of the identified possible data object combinations; identify data object combinations of the identified possible data object combinations having a total weight value less than or equal to the weight value of the at least one resource domain; identify data object combinations, of the identified data object combinations of the possible data object combinations having a total weight value less than or equal to the weight value of the at least one resource domain, having a total score value greater than a first total score value threshold; generate a first set of data object combinations using identified data object combinations, of the identified data object combinations of the possible data object combinations having a total weight value less than or equal to the weight value of the at least one resource domain, having a total score value greater than the first total score value threshold; set a mutation variable to a predetermine value; apply the mutation variable to the first set of data object combinations; select at least two data object combinations of the first set of data object combinations after application of the mutation variable to the first set of data object combinations; identify data objects that appear in each of the at least two data object combinations of the first set of data object combinations; generate, using an artificial intelligence engine configured to use at least one machine learning model configured to identify data object combinations, a second set of data object combinations using the data objects that appear in each of the at least two data object combinations of the first set of data object combinations and each possible combination of data objects that do not appear in at least one data object combination of the at least two data object combinations of the first set of data object combinations; and provide, to a display, output indicating data object combinations of the second set of data object combinations having a total score value above a second total score value threshold.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Implementations of the systems, algorithms, methods, instructions, etc., described herein may be realized in hardware, software, or any combination thereof. The hardware may include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

What is claimed is:

1. A system for dynamically scoring aspects of a data object, the system comprising:
a processor; and
a memory including instructions that, when executed by the processor, cause the processor to:
receive a first data object indicating:
a first value associated with a first value type, the first value corresponding to a first weight value;
a second value associated with the first value type, the second value corresponding to a second weight value;
a third value associated with a second value type, the third value corresponding to a third weight value;
a fourth value associated with the second value type, the fourth value corresponding to a fourth weight value; and
a fifth value corresponding to a third value type;
determine a first sum of a product of the first value and the first weight value plus a product of the second value and the second weight value;
generate a first score based on a result of the first sum divided by a sum of the first weight value and the second weight value;
determine a second sum of a product of the third value and the third weight value plus a product of the fourth value and the fourth weight value;
generate a second score based on a result of the second sum divided by a sum of the third weight value and the fourth weight value;
determine a first data object score for the first data object based on, at least, the first score, the second score, and the fifth value;
identify, using the first data object and the first data object score, data object combinations that include the first data object and at least one other data object, wherein each data object combination has a total weight value that is less than a weight value of a resource domain corresponding to a group of workforce resources specializing in at least one area of expertise, wherein the resource domain is determined using each data object of the data object combinations, and wherein each data object combination is represented by a binary string having a number of digits each representing a data object of the data object combination;
generate a report comprising, at least, the first data object score and at least one other data object score; and
provide, to a display, the report, wherein the first data object score and the at least one other data object score are organized on the report according to a dynamically generated order.

2. The system of claim 1, wherein the first data object further indicates a sixth value associated with a fourth value type and a seventh value associated with the fourth value type, the sixth value corresponding to a fifth weight value and the seventh value corresponding to a sixth weight value.

3. The system of claim 2, wherein the instructions further cause the processor to:
determine a third sum of a product of the sixth value and the fifth weight value plus a product of the seventh value and the sixth weight value; and
generate a third score based on a result of the third sum divided by a sum of the fifth weight value and the sixth weight value.

4. The system of claim 3, wherein the instructions further cause the processor to determine the first data object score further based on the third score.

5. The system of claim 1, wherein the first score corresponds to one of a business valuation and a time criticality.

6. The system of claim 5, wherein the second score corresponds to the other of the business valuation and the time criticality.

7. The system of claim 1, wherein the fifth value corresponds to an amount of effort associated with execution of a project associated with the first data object.

8. The system of claim 1, wherein identifying, using the first data object and the first data object score, data object combinations that include the first data object and at least one other data object includes identifying the data object combinations after applying a mutation variable to a first set of data object combinations, wherein the data object combinations are associated with the first set of data object combinations.

9. A method for dynamically scoring aspects of a data object, the method comprising:
receiving a first data object indicating:
a first value associated with a first value type, the first value corresponding to a first weight value;
a second value associated with the first value type, the second value corresponding to a second weight value;
a third value associated with a second value type, the third value corresponding to a third weight value;
a fourth value associated with the second value type, the fourth value corresponding to a fourth weight value; and
a fifth value corresponding to a third value type;
determining a first sum of a product of the first value and the first weight value plus a product of the second value and the second weight value;
generating a first score based on a result of the first sum divided by a sum of the first weight value and the second weight value;
determining a second sum of a product of the third value and the third weight value plus a product of the fourth value and the fourth weight value;
generating a second score based on a result of the second sum divided by a sum of the third weight value and the fourth weight value;
determining a first data object score for the first data object based on, at least, the first score, the second score, and the fifth value;
identifying, using the first data object and the first data object score, data object combinations that include the first data object and at least one other data object, wherein each data object combination has a total weight value that is less than a weight value of a resource domain corresponding to a group of workforce resources specializing in at least one area of expertise, wherein the resource domain is determined using each data object of the data object combinations, and wherein each data object combination is represented by a binary string having a number of digits each representing a data object of the data object combination;
generating a report comprising, at least, the first data object score and at least one other data object score; and
providing, to a display, the report, wherein the first data object score and the at least one other data object score are organized on the report according to a dynamically generated order.

10. The method of claim 9, wherein the first data object further indicates a sixth value associated with a fourth value type and a seventh value associated with the fourth value type, the sixth value corresponding to a fifth weight value and the seventh value corresponding to a sixth weight value.

11. The method of claim 10, further comprising:
determining a third sum of a product of the sixth value and the fifth weight value plus a product of the seventh value and the sixth weight value; and
generating a third score based on a result of the third sum divided by a sum of the fifth weight value and the sixth weight value.

12. The method of claim 11, further comprising determining the first data object score further based on the third score.

13. The method of claim 9, wherein the first score corresponds to one of a business valuation and a time criticality.

14. The method of claim 13, wherein the second score corresponds to the other of the business valuation and the time criticality.

15. The method of claim 9, wherein the fifth value corresponds to an amount of effort associated with execution of a project associated with the first data object.

16. An apparatus for dynamically scoring aspects of a data object, the apparatus comprising:
a processor; and
a memory including instructions that, when executed by the processor, cause the processor to:
receive a first data object indicating:
a first value associated with a first value type, the first value corresponding to a first weight value;
a second value associated with the first value type, the second value corresponding to a second weight value;
a third value associated with a second value type, the third value corresponding to a third weight value;
a fourth value associated with the second value type, the fourth value corresponding to a fourth weight value; and
a fifth value corresponding to a third value type, the fifth value corresponding to an amount of effort associated with execution of a project associated with the first data object;
determine a first sum of a product of the first value and the first weight value plus a product of the second value and the second weight value;
generate a first score based on a result of the first sum divided by a sum of the first weight value and the second weight value;
determine a second sum of a product of the third value and the third weight value plus a product of the fourth value and the fourth weight value;
generate a second score based on a result of the second sum divided by a sum of the third weight value and the fourth weight value;
determine a first data object score for the first data object based on, at least, the first score, the second score, and the fifth value;
generate a report comprising, at least, the first data object score and at least one other data object score;
identify, using the first data object and the first data object score, data object combinations that include the first data object and at least one other data object, wherein each data object combination has a total weight value that is less than a weight value of a resource domain corresponding to a group of workforce resources specializing in at least one area of expertise, wherein the resource domain is determined using each data object of the data object combinations, and wherein each data object combination is represented by a binary string having a number of digits each representing a data object of the data object combination; and
provide, to a display, the report, wherein the first data object score and the at least one other data object score are organized on the report according to a dynamically generated order.

\* \* \* \* \*